(12) United States Patent
Heavener et al.

(10) Patent No.: US 10,881,462 B2
(45) Date of Patent: Jan. 5, 2021

(54) METHOD OF DETERMINING A CONTOUR OF AN ANATOMICAL STRUCTURE AND SELECTING AN ORTHOPAEDIC IMPLANT TO REPLICATE THE ANATOMICAL STRUCTURE

(71) Applicant: Zimmer, Inc., Warsaw, IN (US)

(72) Inventors: Jackson R. Heavener, Warsaw, IN (US); Justin J. May, Leesburg, IN (US)

(73) Assignee: Zimmer, Inc., Warsaw, IN (US)

(*) Notice: Subject to any disclaimer, the term of this patent is extended or adjusted under 35 U.S.C. 154(b) by 975 days.

(21) Appl. No.: 14/931,156

(22) Filed: Nov. 3, 2015

(65) Prior Publication Data

US 2016/0051334 A1 Feb. 25, 2016

Related U.S. Application Data

(63) Continuation of application No. 12/191,429, filed on Aug. 14, 2008, now Pat. No. 9,179,983.

(60) Provisional application No. 60/955,680, filed on Aug. 14, 2007.

(51) Int. Cl.
*A61B 34/10* (2016.01)
*A61B 34/20* (2016.01)

(52) U.S. Cl.
CPC ........ *A61B 34/10* (2016.02); *A61B 2034/108* (2016.02); *A61B 2034/2068* (2016.02)

(58) Field of Classification Search
CPC ............. A61L 34/10; A61L 2034/2068; A61L 2019/2074
See application file for complete search history.

(56) References Cited

U.S. PATENT DOCUMENTS

| | | | |
|---|---|---|---|
| 4,549,540 | A | 10/1985 | Caspari et al. |
| 4,913,413 | A | 4/1990 | Raab et al. |
| 4,936,862 | A | 6/1990 | Walker et al. |
| 5,030,237 | A | 7/1991 | Sorbie et al. |
| 5,403,319 | A | 4/1995 | Matsen, III et al. |

(Continued)

FOREIGN PATENT DOCUMENTS

| | | |
|---|---|---|
| DE | 2821247 A1 | 11/1979 |
| EP | 1406203 A2 | 4/2004 |

(Continued)

OTHER PUBLICATIONS

"U.S. Appl. No. 12/191,429, Final Office Action dated Aug. 17, 2012", 8 pgs.

(Continued)

*Primary Examiner* — Jerrah Edwards
*Assistant Examiner* — Christine L Nelson
(74) *Attorney, Agent, or Firm* — Schwegman Lundberg & Woessner, P.A.

(57) ABSTRACT

A computer assisted surgery (CAS) system and method for preparing an anatomical structure to receive an orthopaedic implant. The method generally involves the steps of determining a contour of the anatomical structure by using the CAS system to acquire a plurality of points on the anatomical structure and provide a best fit approximation of the anatomical structure based on the plurality of points, selecting an implant to replicate the anatomical structure, and preparing the anatomical structure to receive the implant.

15 Claims, 9 Drawing Sheets

(56) References Cited

U.S. PATENT DOCUMENTS

| | | | |
|---|---|---|---|
| 5,408,409 A | 4/1995 | Glassman et al. | |
| 5,540,696 A | 7/1996 | Booth, Jr. et al. | |
| 5,682,886 A * | 11/1997 | Delp | A61B 17/154 128/920 |
| 5,792,147 A | 8/1998 | Evans et al. | |
| 5,828,813 A | 10/1998 | Ohm | |
| 5,834,759 A | 11/1998 | Glossop | |
| 5,871,018 A | 2/1999 | Delp et al. | |
| 5,921,992 A | 7/1999 | Costales et al. | |
| 6,006,126 A | 12/1999 | Cosman | |
| 6,096,050 A | 8/2000 | Audette | |
| 6,160,264 A | 12/2000 | Rebiere | |
| 6,197,017 B1 | 3/2001 | Brock et al. | |
| 6,205,411 B1 | 3/2001 | Digioia, III et al. | |
| 6,233,504 B1 | 5/2001 | Das et al. | |
| 6,338,716 B1 | 1/2002 | Hossack et al. | |
| 6,348,058 B1 | 2/2002 | Melkent et al. | |
| 6,430,434 B1 | 8/2002 | Mittelstadt | |
| 6,434,507 B1 | 8/2002 | Clayton et al. | |
| 6,450,978 B1 | 9/2002 | Brosseau et al. | |
| 6,470,207 B1 | 10/2002 | Simon et al. | |
| 6,490,467 B1 | 12/2002 | Bucholz et al. | |
| 6,490,475 B1 | 12/2002 | Seeley et al. | |
| 6,491,699 B1 | 12/2002 | Henderson et al. | |
| 6,510,334 B1 | 1/2003 | Schuster et al. | |
| 6,533,737 B1 | 3/2003 | Brosseau et al. | |
| 6,697,664 B2 | 2/2004 | Kienzle, III et al. | |
| 6,701,174 B1 | 3/2004 | Krause et al. | |
| 6,772,026 B2 | 8/2004 | Bradbury et al. | |
| 6,932,842 B1 | 8/2005 | Litschko et al. | |
| 7,024,032 B2 | 4/2006 | Kidd et al. | |
| 7,029,477 B2 | 4/2006 | Grimm | |
| 7,039,225 B2 | 5/2006 | Tanaka et al. | |
| 7,194,295 B2 | 3/2007 | Vilsmeier | |
| 7,234,937 B2 | 6/2007 | Sachdeva et al. | |
| 7,242,999 B2 | 7/2007 | Wang | |
| 7,275,023 B2 | 9/2007 | Chen et al. | |
| 7,587,075 B1 | 9/2009 | Stefan et al. | |
| 7,603,192 B2 | 10/2009 | Martin et al. | |
| 7,604,665 B2 | 10/2009 | Iannotti et al. | |
| 7,634,306 B2 | 12/2009 | Sarin et al. | |
| 7,646,901 B2 | 1/2010 | Murphy et al. | |
| 7,715,602 B2 | 5/2010 | Richard | |
| 9,179,983 B2 | 11/2015 | Heavener et al. | |
| 2002/0068942 A1 | 6/2002 | Neubauer et al. | |
| 2003/0033127 A1 | 2/2003 | Lett | |
| 2003/0130665 A1 | 7/2003 | Pinczewski et al. | |
| 2003/0225415 A1 | 12/2003 | Richard | |
| 2004/0102866 A1 | 5/2004 | Harris et al. | |
| 2004/0111183 A1 | 6/2004 | Sutherland et al. | |
| 2004/0122305 A1 | 6/2004 | Grimm et al. | |
| 2004/0146830 A1 | 7/2004 | Weinstein | |
| 2004/0152955 A1 | 8/2004 | McGinley et al. | |
| 2004/0153062 A1 * | 8/2004 | McGinley | A61B 17/15 606/53 |
| 2004/0157188 A1 | 8/2004 | Luth et al. | |
| 2004/0230199 A1 | 11/2004 | Jansen et al. | |
| 2005/0076521 A1 | 4/2005 | Said | |
| 2005/0119564 A1 | 6/2005 | Rosholm et al. | |
| 2005/0197814 A1 | 9/2005 | Aram et al. | |
| 2005/0198849 A1 | 9/2005 | Goeggelmann et al. | |
| 2005/0234332 A1 | 10/2005 | Murphy | |
| 2006/0094951 A1 | 5/2006 | Dean et al. | |
| 2006/0100498 A1 | 5/2006 | Boyce et al. | |
| 2006/0100832 A1 | 5/2006 | Bowman | |
| 2006/0161051 A1 | 7/2006 | Terrill-Grisoni et al. | |
| 2006/0204067 A1 | 9/2006 | Tuma et al. | |
| 2006/0216681 A1 | 9/2006 | Walker et al. | |
| 2006/0229624 A1 | 10/2006 | May et al. | |
| 2007/0066893 A1 | 3/2007 | Eriksen et al. | |
| 2007/0066917 A1 * | 3/2007 | Hodorek | A61B 90/36 600/595 |
| 2007/0123894 A1 | 5/2007 | Claypool et al. | |
| 2007/0156066 A1 | 7/2007 | Mcginley et al. | |
| 2007/0156157 A1 | 7/2007 | Nahum et al. | |
| 2007/0203605 A1 | 8/2007 | Melton et al. | |
| 2007/0255288 A1 | 11/2007 | Mahfouz et al. | |
| 2007/0274442 A1 | 11/2007 | Gregory et al. | |
| 2008/0009954 A1 | 1/2008 | Mueller et al. | |
| 2008/0163344 A1 | 7/2008 | Yang | |
| 2008/0167547 A1 | 7/2008 | Bova et al. | |
| 2008/0183086 A1 * | 7/2008 | Song | A61B 5/0452 600/508 |
| 2008/0273775 A1 | 11/2008 | Hilbelink | |
| 2009/0089034 A1 | 4/2009 | Penney et al. | |

FOREIGN PATENT DOCUMENTS

| | | |
|---|---|---|
| FR | 2776176 A1 | 9/1999 |
| WO | WO-9423605 A1 | 10/1994 |
| WO | WO-9937220 A1 | 7/1999 |
| WO | WO-0003210 A1 | 1/2000 |
| WO | WO-03030738 A1 | 4/2003 |
| WO | WO-2004017842 A2 | 3/2004 |
| WO | WO-2004019792 A1 | 3/2004 |
| WO | WO-2008015565 A2 | 2/2008 |

OTHER PUBLICATIONS

"U.S. Appl. No. 12/191,429, Final Office Action dated Oct. 6, 2014", 8 pgs.

"U.S. Appl. No. 12/191,429, Non Final Office Action dated Apr. 24, 2014", 8 pgs.

"U.S. Appl. No. 12/191,429, Non Final Office Action dated Dec. 23, 2011", 7 pgs.

"U.S. Appl. No. 12/191,429, Notice of Allowance dated Jul. 8, 2015", 5 pgs.

"U.S. Appl. No. 12/191,429, Response filed Mar. 29, 2012 to Non Final Office Action dated Dec. 23, 2011", 11 pgs.

"U.S. Appl. No. 12/191,429, Response filed Apr. 6, 2015 to Final Office Action dated Oct. 6, 2014", 15 pgs.

"U.S. Appl. No. 12/191,429, Response filed Sep. 23, 2014 to Non-Final Office Action dated Apr. 24, 2014", 13 pgs.

"U.S. Appl. No. 12/191,429, Response filed Nov. 19, 2012 to Final Office Action dated Aug. 17, 2012", 16 pgs.

"Biomet Orthopedics, Inc. Product Detail Signature Personalized Patient Care", (2008), 1 pg.

"Biomet Orthopedics, Inc., Signature Personalized Arthritis Care", (2008, 2009), 2 pgs.

"Minimally Invasive Surgical Technique (MIS), Intramedullary Surgical Approach", MIS, the MIG Unicompartmental Knee, Zimmer, (2002), 26 pgs.

"Surgical Technique—Nexgen Complete Knee Solution for the Legacy Knee LPS-Flex Fixed Bearing Knee", Zimmer, Inc., (2004, 2007), 12 pgs.

"Webpage and Product Brochure", Biomet Orthopedics, Signature Personalized Arthritis Care and Signature Personalized Patient Care, [Online] Retrieved From Internet: <http://www.biomet.com/orthopedics/productDetail.cfm?category=2&product=242>, (Sep. 11, 2008).

Horn, "Closed-form solution of absolute orientation using unit quaternions", Reprinted from Journal of the Optical Society of America A. vol. 4, (Apr. 1987), 629-642.

Kienzle, et al., "Total Knee Replacement", IEEE Engineering in Medicine and Biology Magazine, vol. 14, No. 3, (May 1, 1995), 301-306.

Mahaluxmivala, et al., "The effect of surgeon experience on component positioning in 673 press FIT condylar posterior cruciate—sacrificing totla knee arthroplasties", Article The Journal of Arthroplasty vol. 16, No. 5 (2001), 635-340.

Perlick, et al., "Navigation in total knee arthroplasty Ct-Based implantation compared with the conventional technique", Article Acta Orthop Scand 2004: 75, 464-470.

Perlick, et al., "Usability of an image based navigation system in reconstruction of leg alignment in total knee arthroplasty - Results of a prospective study", Article Biomedizinische Technik Band 48, Heft Dec. 2003, 339-343.

(56) References Cited

OTHER PUBLICATIONS

Taylor, et al., "Robotic Total Hip Replacement Surgery in Dogs", Medical Applications of Robotics, IEEE Engineering in Medicine & Biology Society 11th Annual International Conference, (1989), 3 pgs.

Testi, Debora, et al., "JIDE: a new software for computer-aided design of hip prosthesis", Computer Methods and Programs in Biomedicine V.75 No. 3, (2004), 213-220.

Tucker, et al., "Point Cloud to CAD Model Registration Methods in Manufacturing Inspection", Journal of Computing and Information Science in Engineering Technology Review, vol. 6, (Dec. 2006), 418-421.

Viceconti, Marco, et al., "An automated method to position prosthetic components within multiple anatomical spaces", Computer Methods and Programs in Biomedicine V. 70 No. 2, (2003), 121-127.

Viceconti, Marco, et al., "TRI2SOLIDE: an application of reverse engineering methods to the creation of CAD models of bone segments", Computer Methods and Programs in Biomedicine, V.56, No. 3, Istituti Ortopedici Rizzoli, Bologna, Italy, (1998), 211-220.

\* cited by examiner

METHOD OF DETERMINING A CONTOUR OF AN ANATOMICAL STRUCTURE AND SELECTING AN ORTHOPAEDIC IMPLANT TO REPLICATE THE ANATOMICAL STRUCTURE

RELATED APPLICATIONS

This application is a continuation of U.S. patent application Ser. No. 12/191,429, filed Aug. 14, 2008, now issued as U.S. Pat. No. 9,179,983, which claims the benefit of U.S. Provisional Patent Application Ser. No. 60/955,680, filed Aug. 14, 2007, the disclosures of which are expressly incorporated by reference herein.

BACKGROUND

1. Field of the Disclosure

The present disclosure relates to a computer assisted surgery system and method for preparing an anatomical structure to receive an implant.

2. Description of the Related Art

Orthopaedic procedures for the replacement of at least a portion of a bone or other anatomical structure of a patient typically require preparing the anatomical structure to receive an implant. Such preparation may involve determining a desired size, type, and shape of the implant based on the size and shape of the anatomical structure. For example, determination of the type and size of implants for a total knee arthroplasty procedure are typically based on sizing measurements taken of the knee, e.g., anterior/posterior and medial/lateral dimensions, as well as by the location of the mechanical axis of the femur.

SUMMARY

The present disclosure provides a computer assisted surgery (CAS) system and method for preparing an anatomical structure to receive an orthopaedic implant and/or to assess and evaluate an anatomical structure. In an exemplary embodiment, the method generally involves the steps of determining a contour of the anatomical structure by using the CAS system to acquire a plurality of points on the anatomical structure, provide a best fit approximation of the anatomical structure based on the plurality of points, selecting an implant to replicate the anatomical structure, and preparing the anatomical structure to receive the implant.

In one form thereof, the present disclosure provides a method of orthopaedic surgery for use with an anatomical structure, including the steps of acquiring a plurality of data points from the anatomical structure by contacting a pointer device to the anatomical structure at a plurality of locations; using the plurality of data points to calculate a best fit approximation of a contour of the anatomical structure; selecting an orthopaedic implant substantially matching the contour of the anatomical structure; preparing the anatomical structure to receive the orthopaedic implant; and implanting the orthopaedic implant in the anatomical structure.

In an exemplary embodiment of the present disclosure, a method of selecting a placement of an implant for an orthopaedic surgery is provided. The method comprising the steps of identifying a region of an anatomical structure for replacement by said implant; receiving a plurality of data points corresponding to a contour of said region of said anatomical structure; selecting said implant from a library of implants, said implant being selected based on said contour of said region of said anatomical structure; and providing a proposed placement of said implant relative to said anatomical structure. In an example, the method further comprises the step of providing an indication of a fit between a contour of said implant and said contour of said region of said anatomical structure. In another example, the method further comprises the step of receiving a revised placement of said implant relative to said anatomical structure. In yet another example, the step of receiving said plurality of data points includes the steps of receiving an indication that a pointer device is positioned at a first position; determining a first coordinate of said first position; and determining a second coordinate of a second position. In a variation thereof, the step of determining said second coordinate of said second position is performed in response to receiving an indication that said pointer device is positioned at said second position. In another variation, the step of determining said second coordinate of said second position including the step of waiting a predetermined time interval from determining said first coordinate of said first position, said pointer device being moved by an operator during said predetermined time interval. In a further example, the step of receiving said plurality of data points includes the steps of obtaining preoperative representations of said region of said anatomical structure; and determining said plurality of data points from said preoperative representations of said region of said anatomical structure. In still another example, said contour is determined from a fitting of said plurality of data points to a surface. In still yet anther example, the method further comprises the step of receiving at least one constraint on said proposed placement of said implant relative to said anatomical structure. In a variation thereof, said at least one constraint is related to an orientation of said implant relative to said anatomical structure. In another variation, said at least one constraint is related to a location of a top surface of said implant relative to said anatomical structure. In yet another example, the step of selecting said implant from said library of implants includes the step of receiving a selection of said implant from a user input device. In still another example, the step of selecting said implant from said library of implants includes the step of comparing a contour of each of a plurality of implants to said contour of said anatomical structure, said implant being selected in response to said contour of said implant most closely matching said contour of said anatomical structure. In another example, the method further comprises the step of generating a resection plan for said anatomical structure based on said implant.

In another exemplary embodiment of the present disclosure, a method of selecting a placement of an implant for an orthopaedic surgery is provided. The method comprising the steps of identifying a region of an anatomical structure for replacement by said implant; determining a contour of said region of said anatomical structure; for each of a plurality of implants determining a fit between a contour of said respective implant and said contour of said anatomical structure; and receiving an indication of a selected implant from said plurality of implants. In an example, said plurality of implants is selected from a library of implants. In a variation thereof, each of said plurality of implants are selected based on satisfying at least one constraint related to said anatomical structure. In another variation thereof, the method further comprises the step of for each of said plurality of implants determining a resection plan for said anatomical structure, wherein said selected implant is selected from said plurality of implants based on said resection plan for said selected implant.

In a further exemplary embodiment of the present disclosure, a method of selecting the placement of an implant for an orthopaedic surgery is provided. The method comprising the steps of identifying a region of an anatomical structure for replacement by said implant; determining a contour of said region of said anatomical structure; obtaining a blank implant for implantation in said anatomical structure; determining a resection plan for said blank implant; and machining a top portion of said blank implant to generally match said contour of said region of said anatomical structure. In an example, the method further comprises the steps of resecting said anatomical structure based on said resection plan; and implanting said blank implant in said anatomical structure. In a variation thereof, the step of implanting said blank implant in said anatomical structure occurs prior to the step of machining said top portion of said blank implant to match said contour of said region of said anatomical structure. In a further variation thereof, the step of implanting said blank implant in said anatomical structure occurs subsequent to the step of machining said top portion of said blank implant to match said contour of said region of said anatomical structure.

In yet another exemplary embodiment of the present disclosure, a method of selecting a placement of an implant for an orthopaedic surgery is provided. The method comprising the steps of identifying a region of a current anatomical structure for replacement by said implant; determining a current contour of said region of said current anatomical structure; comparing said current contour of said current anatomical structure to a library of contours of anatomical structures; selecting a first contour of a first anatomical structure from said library of contours of anatomical structures; and selecting a first implant for implantation in said current anatomical structure, said first implant having been implanted in said first anatomical structure. In an example, a placement of said first implant relative to said current anatomical structure corresponds to a placement of said first implant relative to said first anatomical structure. In a variation thereof, the method further comprises the step of determining a resection plan for said first implant for said current anatomical structure. In another variation, said first contour is selected based on said first contour being closest to said current contour than the remainder of said library of contours. In a further variation, said first contour is selected based on said first contour having a first constraint which matches a constraint for said current anatomical structure. In yet a further variation, said first contour is selected based on said first contour being closest to said current contour than the remainder of said library of contours.

In still another exemplary embodiment of the present disclosure, a method of orthopaedic surgery for use with an anatomical structure is provided. The method comprising the steps of acquiring a plurality of data points from said anatomical structure; determining an approximation of a contour of said anatomical structure based on said plurality of data points; selecting a first orthopaedic implant from a plurality of orthopaedic implants for said anatomical structure based on said determined contour of said anatomical structure; preparing said anatomical structure to receive said first orthopaedic implant; and coupling said first orthopaedic implant to said anatomical structure. In an example, said acquiring step comprises contacting a pointer device to said anatomical structure at a plurality of locations. In another example, said acquiring step comprises obtaining said data points based on a preoperative plan.

In yet still a further exemplary embodiment of the present disclosure, a method of orthopaedic surgery for use with an anatomical structure is provided. The method comprising the steps of acquiring a plurality of data points from said anatomical structure; using said plurality of data points to calculate a best fit approximation of a contour of said anatomical structure; selecting an orthopaedic implant substantially matching said contour of said anatomical structure; preparing said anatomical structure to receive said orthopaedic implant; and implanting said orthopaedic implant in said anatomical structure. In an example, said acquiring step comprises contacting a pointer device to said anatomical structure at a plurality of locations. In another example, said acquiring step comprises obtaining said data points based on a preoperative plan.

Additional features and advantages of the present invention will become apparent to those skilled in the art upon consideration of the following detailed description of illustrative embodiments exemplifying the best mode of carrying out the invention as presently perceived.

BRIEF DESCRIPTION OF THE DRAWINGS

The above-mentioned and other features of the disclosure, and the manner of attaining them, will become more apparent and will be better understood by reference to the following description of embodiments of the disclosure taken in conjunction with the accompanying drawings, wherein.

Corresponding reference characters indicate corresponding parts throughout the several views. The exemplifications set out herein illustrate embodiments of the disclosure and such exemplifications are not to be construed as limiting the scope of the invention in any manner.

DETAILED DESCRIPTION

Figure 1:
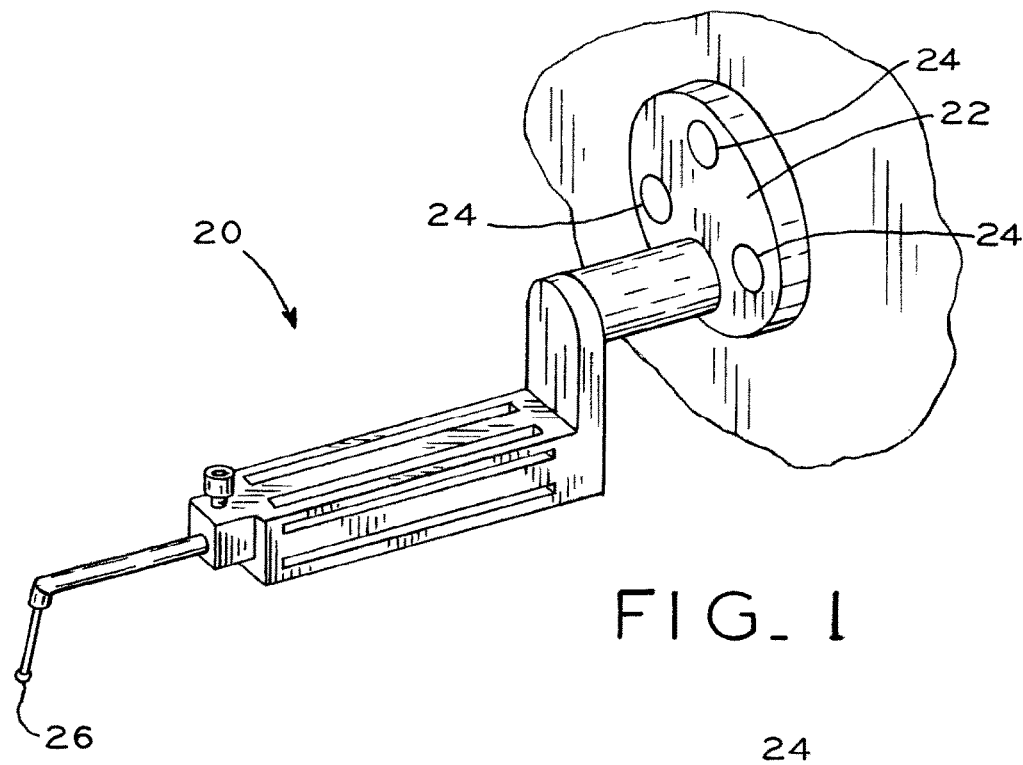
FIG. 1 is a perspective view of a pointer device for use in obtaining a plurality of points on an anatomical structure.

Referring now to FIG. 1, pointer probe or device 20 according to one embodiment of the present disclosure is shown. Pointer device 20 may include adapter portion 22 which may be used to operably couple pointer device 20 to a computer assisted surgery (CAS) system, for example, a robotic surgical system or haptic device, such as the system and device described in U.S. patent application Ser. No. 11/610,728, entitled AN IMAGELESS ROBOTIZED DEVICE AND METHOD FOR SURGICAL TOOL GUIDANCE, filed Dec. 14, 2006, assigned to the assignee of the present application, the disclosure of which is hereby expressly incorporated herein by reference, and such as the system and device described in U.S. patent application Ser.

No. 12/020,003, entitled INSTRUMENTED LINKAGE SYSTEM, filed Jan. 25, 2008, the disclosure of which is expressly incorporated by reference herein. Accordingly, adapter portion 22 may be configured to be coupled to such a device and may include fastener receiving holes 24 through which fasteners (not shown) may extend to secure pointer device 20 to an arm of the device. Pointer device 20 may include interface structure 26 for interfacing with an anatomical structure, as described below. Alternatively, pointer device 20 may be adapted and configured to couple with any image-guided system, any imageless CAS system, any non-robotic system, any robotic system, as well as any system based on optical, electromagnetic, or radiofrequency tracking technology.

Figure 2:
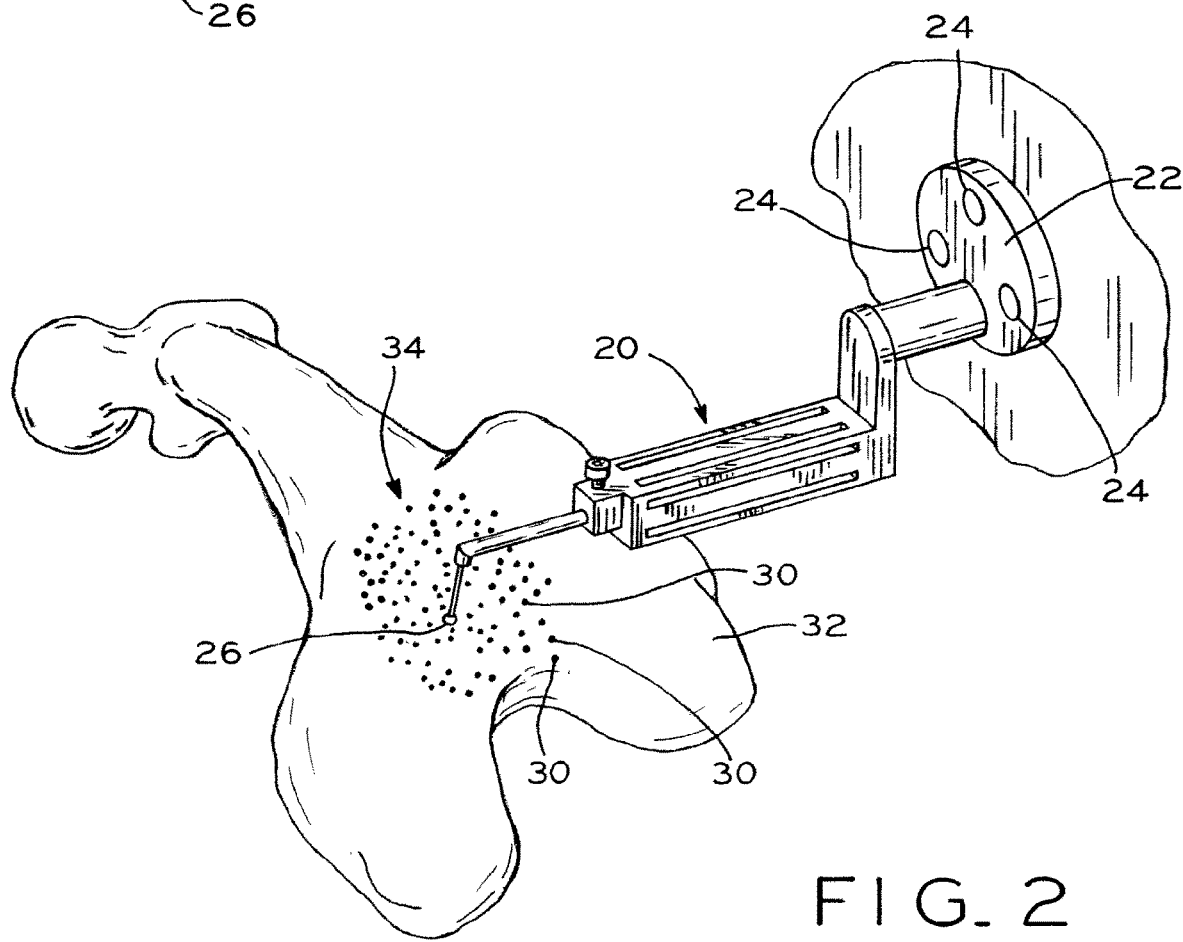
FIG. 2 is a perspective view of the pointer device of FIG. 1, further illustrating the step of identifying a plurality of points on a distal femur.

In operation and referring to FIG. 2, pointer device 20 may be used to identify a plurality of points 30 on an anatomical structure, such as distal femur 32, for example. Method 100 (FIG. 4) depicts an exemplary method of the present disclosure. A surgeon or other user may grasp pointer device 20 and move interface structure 26 thereof into contact with distal femur 32, thereby identifying a point 30 in step 102 (FIG. 4) of a region for replacement by an implant and surrounding area. Contacting distal femur 32 may include physical contact with interface structure 26 or remote contact via a light-emitting device or other similar non-physical projection extending from interface structure 26 to contact distal femur 32. The user may verify identification of point 30 in the CAS system using a foot pedal or other suitable verification device. The user may then drag pointer device 20 across a surface of distal femur 32 such that interface structure 26 maintains contact with distal femur 32. The CAS system may be configured to periodically obtain coordinates of the location of interface structure 26. This may be done in rapid succession such that interface structure 26 "paints" distal femur 32 and the CAS system records a plurality of points 30 generally corresponding to the contour of distal femur 32. In an exemplary embodiment, the CAS system may be configured to obtain points 30 at intervals between 0.1 and 0.5 milliseconds. When interface structure 26 touches each point 30, encoders or other position identification devices in the arm of the CAS system may be used to record the location of interface structure 26 in a three-dimensional coordinate system. In another embodiment, the arm of the device and/or pointer device 20 may include tracking devices to identify the location of interface structure 26 in the three-dimensional coordinate system. The tracking devices may be based on optical tracking technology such as infrared tracking, radiofrequency tracking technology, and/or electromagnetic tracking technology, any of which may be used to triangulate the position of interface structure 26 in the three-dimensional coordinate system.

In an exemplary embodiment, the user identifies points 30 in a general area defined by patello-femoral groove 34 of distal femur 32. The CAS system may correlate each point 30 to a three-dimensional coordinate system based on the location of interface structure 26 and pointer device 20. In an alternative embodiment, the user may use interface structure 26 to contact distal femur 32 at a plurality of locations to define points 30 in a manner which does not maintain contact between interface structure 26 and distal femur 32 at all times. In yet another embodiment, distal femur 32 may have points 30 defined by a preoperative image, such as a CT scan, MRI scan, ultrasound data, x-ray data, and other imaging techniques. Other exemplary point cloud collection techniques include optical scanning and LADAR (Laser and Distance Ranging).

Figure 4:
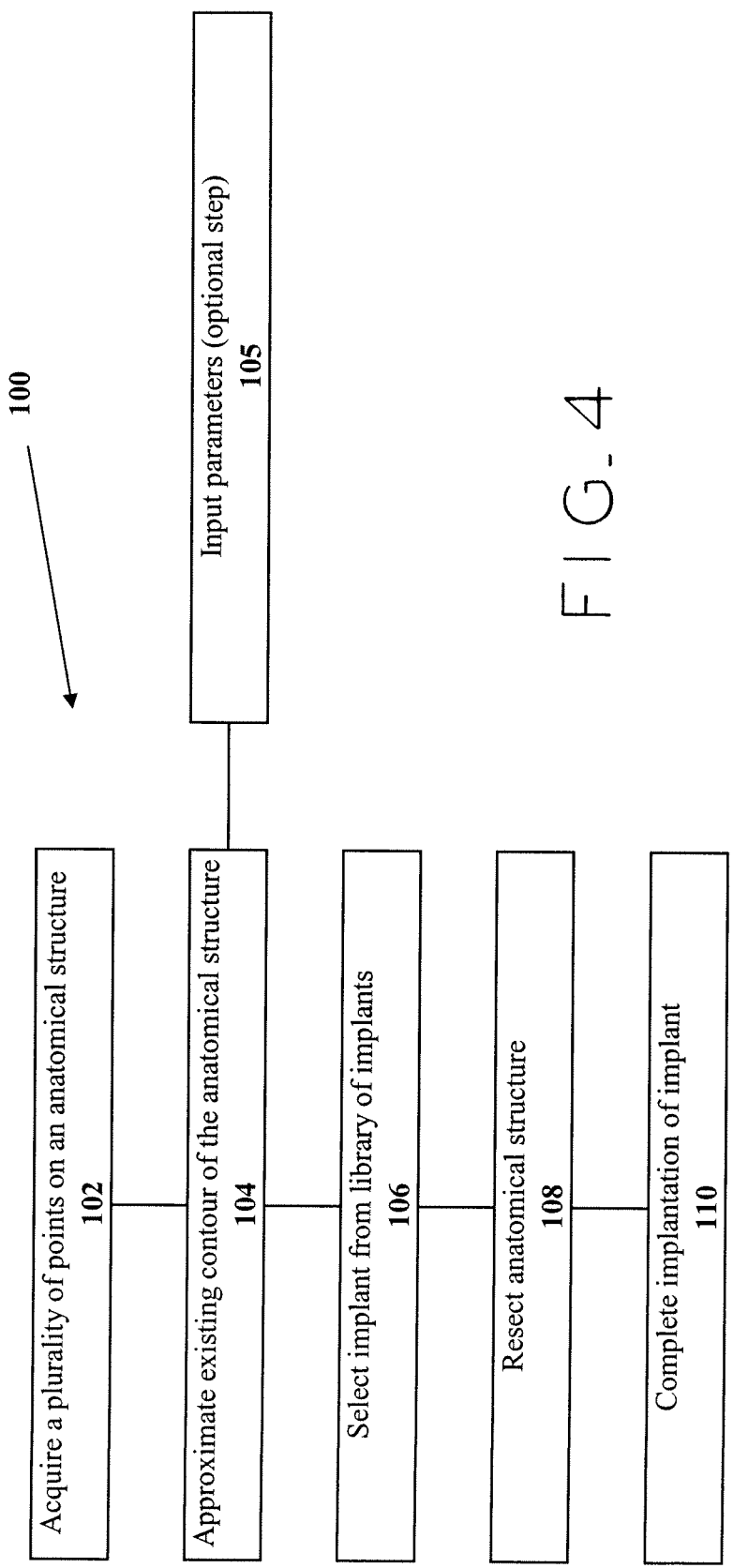
FIG. 4 is a diagrammatic view of a method according to an exemplary embodiment of the present disclosure.

As shown in FIG. 4, the CAS system then uses the plurality of points 30 and approximates a contour of patello-femoral groove 34 of distal femur 32 using a best fit approximation in step 104. An exemplary best fit approximation is a least squares fitting to a surface or other suitable fitting methods. A representation of the anatomical structure is stored as represented by block 107.

In this manner, the CAS system approximates the contour of the existing anatomy of distal femur 32 without requiring any sizing measurements of distal femur 32, such as a distance between a medial condyle and a lateral condyle of distal femur 32, for example. Moreover, the approximation of the contour of distal femur 32 may be completed without defining the mechanical axis of the femur or any other axis associated therewith. When performing the best fit approximation, the CAS system may be configured to permit consideration of parameters, such as bone defects, a desired resection depth, a desired resection area, fitness of various implants, alignment with axes such as a mechanical or anatomical axis, or alignment with other bony landmarks, to be utilized by the software of the CAS system when approximating the contour of distal femur 32, as shown by optional step 105 in FIG. 4. For example, the user may input parameters associated with potential problematic areas of a resultant implant used on distal femur 32, as described below. In one embodiment, potential bone defects may be avoided by interface structure 26 during identification of points 30 and such bone defects may be parameters considered by the CAS system during approximation of the contour of distal femur 32. In another embodiment, bone defects are contacted by interface structure 26 such that a depth of any bone defect is verified and the CAS system can accordingly provide a resection plan which eliminates the bone defect after resection of the bone.

Once the contour of the anatomical structure has been approximated, the CAS system then presents the user with a library of implants, as shown by step 106 in FIG. 4. The library of implants may include implants which will accommodate the best fit approximation of the anatomical structure identified in step 104, described above, i.e., the user will select an implant from the library that most closely replicates the best fit approximation of the contour of the existing anatomical structure such that the existing anatomy is replicated with the chosen implant. The user may then select this implant from the library for subsequent implantation. In an alternative embodiment, step 105 may be used in conjunction with step 106 which allows the user of the CAS system to adjust various parameters, such as desired resection depth, desired resection area, or a desired outcome, for example, to correctly choose the implant. The CAS system may provide visual feedback to the user to evaluate the fit of the chosen implant prior to any resections or implantation. At this point, the surgeon may input various parameters to evaluate the fit of the chosen implant.

In step 108 (FIG. 4), the CAS system then facilitates resection of the anatomical structure to accommodate the chosen implant based on the chosen implant and the best fit approximation of the anatomical structure. In an exemplary embodiment, the CAS system manipulates pointer device 20, which may include a cutting guide, into a desired position relative to the anatomical structure. The CAS system may use software programmed to position pointer device 20 based on the foregoing information about the anatomical structure and desired implant obtained in steps 102, 104, 105, and 106. In one embodiment, steps 106 and 108 in which the user selects an implant from the library of implants and the CAS system facilitates resection of the anatomical structure may be integrated into a single, iterative process. For example, a user may select more than one desired implant and facilitate resection plans for each implant simultaneously. The user may then go back to step 106 and select one of the desired implants based on the resection plans identified in step 108. Finally, in step 110 (FIG. 4), the CAS system then may facilitate implantation of the chosen implant into the anatomical structure.

Figure 3:
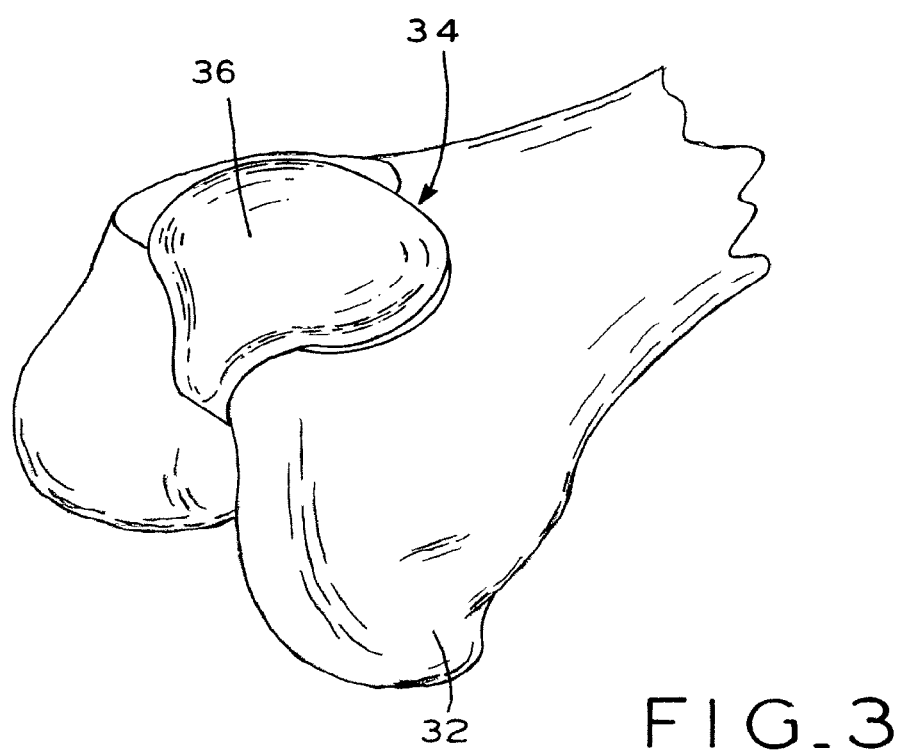
FIG. 3 is a perspective view of a distal femur, further illustrating a patello-femoral implant.

In an exemplary embodiment shown in FIG. 3, the chosen implant may be a patello-femoral implant 36 which corresponds to an implantation site associated with patello-femoral groove 34. For example, in an exemplary embodiment, patello-femoral implant 36 may be any patello-femoral implant described in U.S. patent application Ser. No. 11/671,643, entitled Femoral Trochlea Prostheses, filed on Feb. 6, 2007, and U.S. patent application Ser. No. 11/671,645, entitled Femoral Trochlea Prostheses, filed on Feb. 6, 2007, both of which are assigned to the assignee of the present application, the disclosures of which are hereby expressly incorporated herein by reference. As shown in FIG. 3, patello-femoral implant 36 may be utilized and may provide an appropriate contour match between distal femur 32 and patello-femoral implant 36, i.e., such that no protruding portions of patello-femoral implant 36 are present which may impair the articulation of patello-femoral implant 36 with any other portion of the knee joint during use, as described in the above-incorporated U.S. patent application Ser. No. 11/671,643 and Ser No. 11/671,645.

Although described throughout as using method 100 on a patello-femoral groove, method 100 is equally applicable to approximating a best fit contour of any anatomical structure, particularly those having a relatively small area. For example, method 100 may used in a unicondylar knee replacement surgery in which a medial or lateral condyle of a femur is prepared to receive a unicondylar implant, in a partial femoral head surface replacement surgery in which only a small portion of the femoral head is prepared to receive a partial femoral head implant, or a bicompartmental knee surgery.

Figure 5:
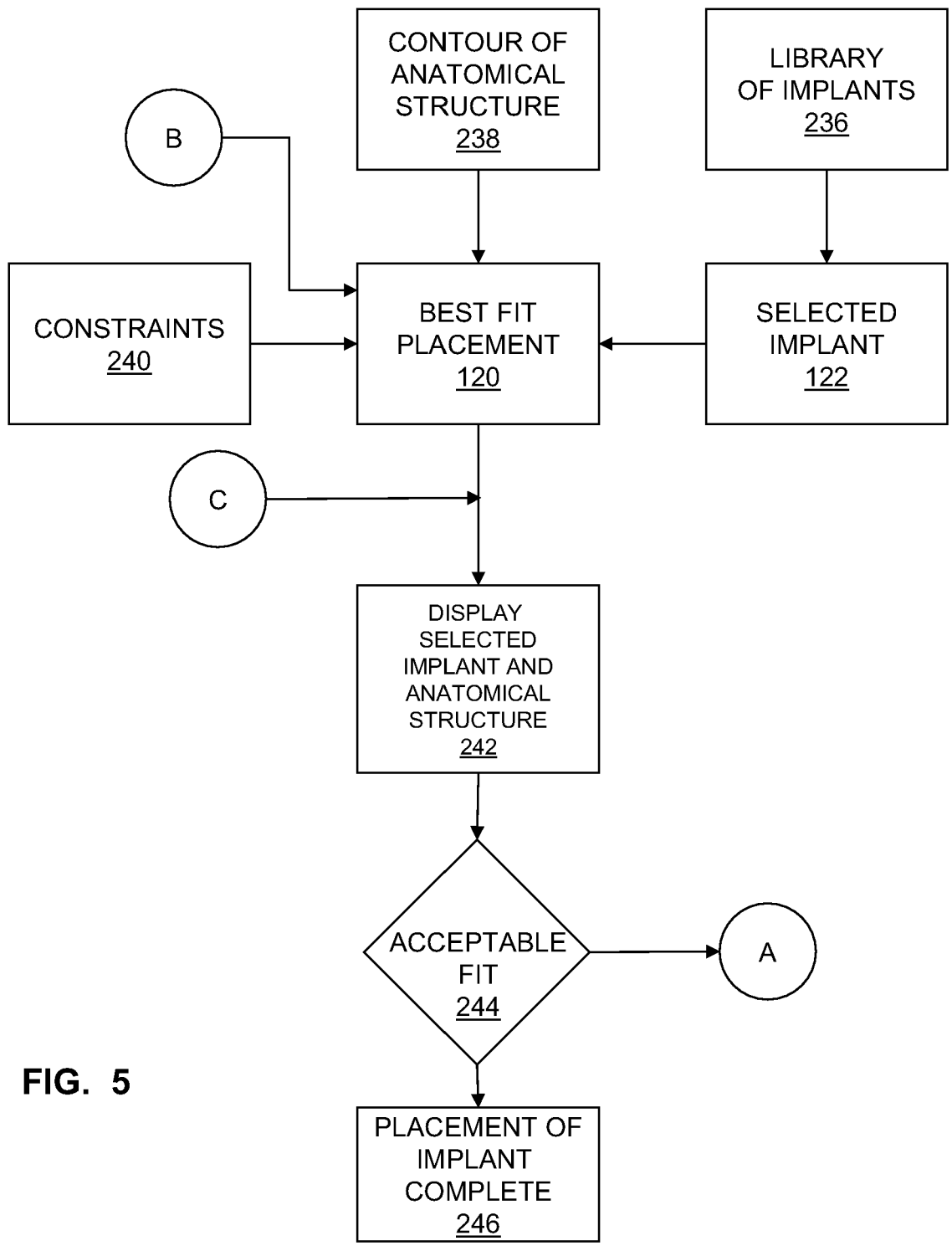
FIGS. 5 and 6 represent a method of locating an implant relative to the a current anatomical structure.
Figure 6:
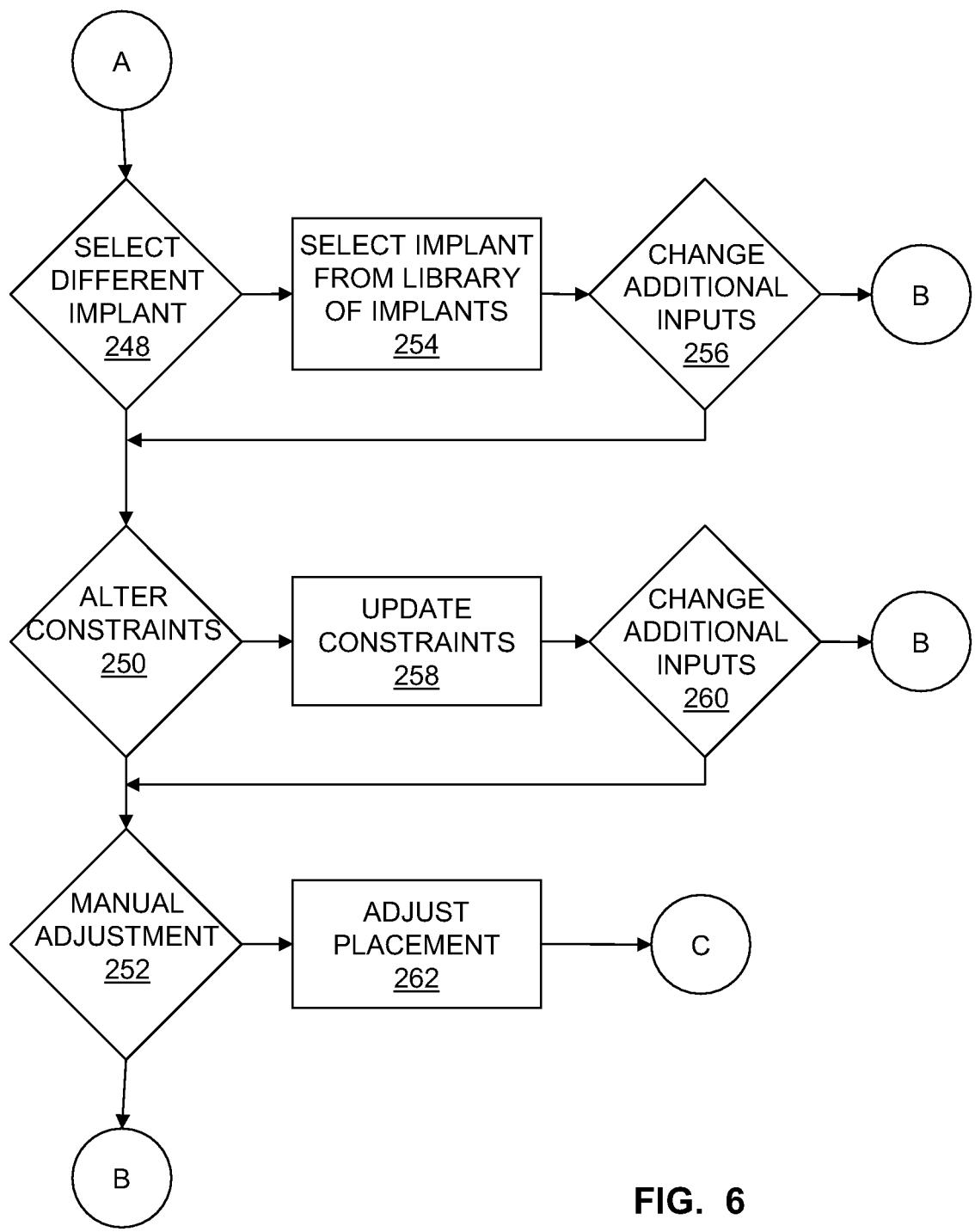
Figure 7:
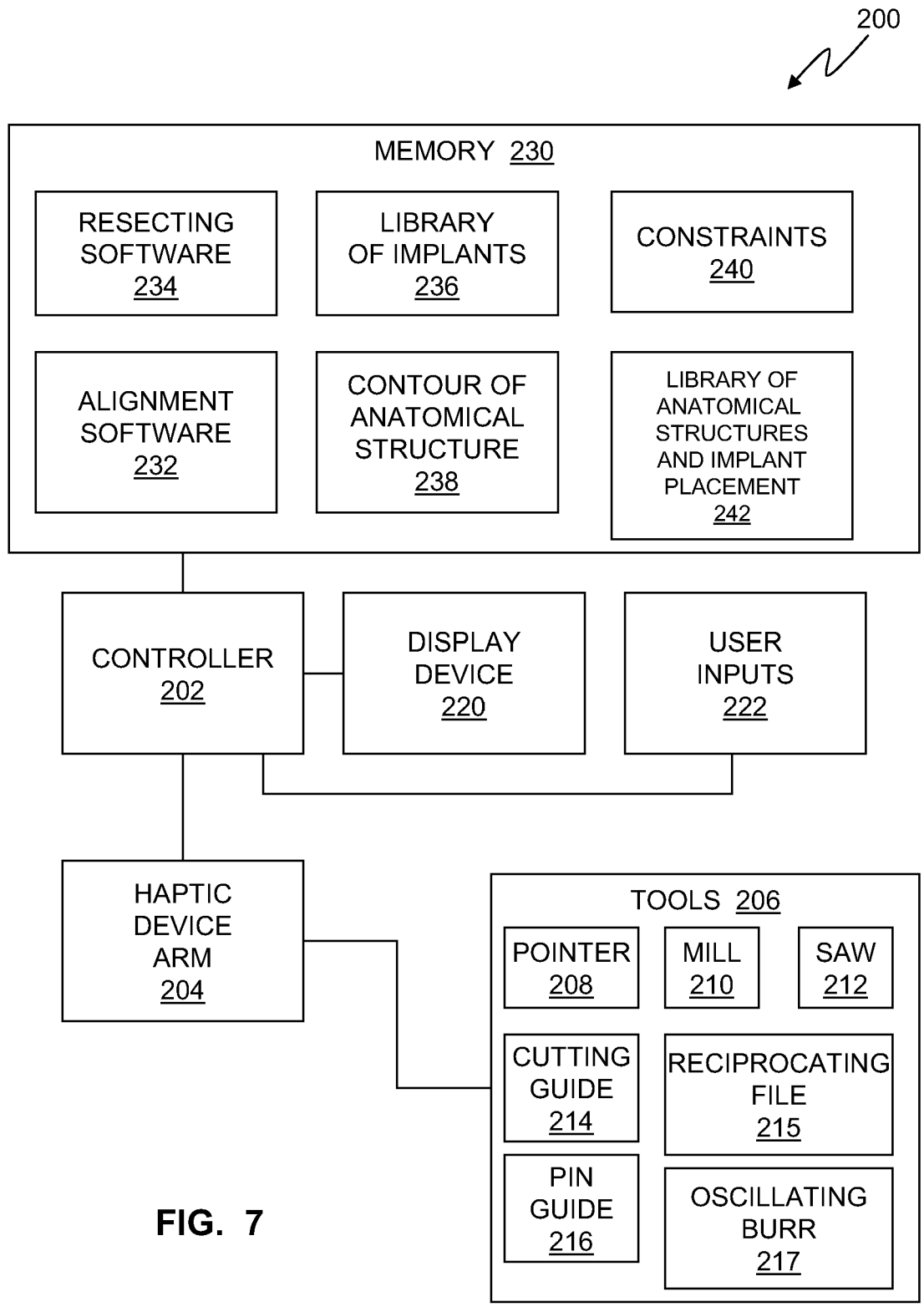
FIG. 7. represents an exemplary CAS system.

Referring to FIGS. 5 and 6, a process for the selection of an implant and the positioning of the implant relative to the anatomical structure through a CAS system 200 is presented. Referring to FIG. 7, CAS system 200 is represented. CAS system 200 includes a controller 202 which is coupled to a haptic device arm 204 and controls the operation of the haptic device arm 204. The haptic device arm 204 may have a plurality of tools 206 attached to an end of the arm. Exemplary tools 206 include a pointer 208 (such as pointer device 20), a mill tool 210, a saw tool 212, a cutting guide tool 214, a reciprocating file 215, a pin guide tool 216, an oscillating burr 217, and other suitable tools. In one embodiment, a cutting guide 214 and/or a pin guide tool 216 may be custom made for the contour of the anatomical structure.

In one embodiment, controller 202 includes a no-fly zone for use with mill tool 210 and saw tool 212. With the no-fly zone, these cutting tools are disabled unless they are placed in a region which controller 202 has identified for removal through resection software 234. As such, with a no-fly zone a surgeon could resect the bone freehand because the tool would be active only when it is in a region to be cut.

Controller 202 is further coupled to a display device 220 to display various items to a user of CAS system 200, such as a comparison of the contour of the anatomical structure to a proposed placement of an implant. Controller 202 is further coupled to user input devices 222 to receive input from a user of CAS system 200. Exemplary user input devices include a mouse, a keyboard, a touch screen, a foot pedal, and other suitable devices for interfacing with a human operator.

Controller 200 has access to a memory 230. Memory 230 may be a single memory device or a collection of many memory devices. Memory 230 may be local relative to controller 202, available across a network, or a combination of local and available across a network.

Memory 230 includes alignment software 232 which performs the fitting methods and alignment methods discussed herein and resecting software 234 which develops a resection plan for a proposed placement of a selected implant. Memory 230 also includes a library of implants 236 which includes information descriptive of a plurality of implants, a contour of the current anatomical structure 238, constraints 240 placed on the implant to be used with the current anatomical structure, and a library of anatomical structures and implant placements 242.

Returning to FIG. 5, a best fit placement of the implant based on a fitting routine, as represented by block 120, is represented. The best fit is based on a selected implant 122 selected from a library of implants 236, the contour of the anatomical structure 238, and one or more constraints 240. The best fit placement may be the registration of two point clouds, one corresponding to the anatomical structure contour and one corresponding to a top surface contour of the implant.

In one embodiment, the best fit placement is performed by an iterative fitting routine. Exemplary iterative fitting routines include 'Least Sum of Squares of Errors' method and "Iterative Closest Point" method. In one embodiment, the best fit placement is performed by a closed form fitting method. An exemplary closed form fitting method is described in Horn, "Closed-form solution of absolute orientation using unit quaterions," Journal of the Optical Society of America, Vol. 4, pages 629-642 (1987), the disclosure of which is expressly incorporated by reference herein.

Controller 202 provides a representation of selected implant 122 and current anatomical structure 238 on display device 220, as represented by block 242. In one embodiment, the displayed representation provides an indication of the mismatch between a contour of selected implant 122 and current anatomical structure 238. An operator of CAS system 200 may then determine whether the proposed placement of the implant is acceptable or not, as represented by block 244. If acceptable, then the proposed placement of the implant is complete, as represented by block 246, and a resection plan is determined for the proposed placement by resecting software 234. In one embodiment, the resection plan is determined prior to a determination of whether the proposed placement is acceptable and is one of the factors in determining if the proposed placement is acceptable.

If the proposed placement is not acceptable, then a determination is made whether to select a different implant, as represented by block 248, whether to alter constraints on the placement of the implant, as represented by block 250, or to manually adjust the placement of the implant relative to the anatomical structure, as represented by block 252.

If the user selects to select a different implant, then another implant is selected from the library of implants, as represented by block 254. In one embodiment, the user manually selects the different implant through user inputs 222. In one embodiment, alignment software 230 selects the different implant from the library of implants. Once the different implant is selected, the user is prompted to determine if additional changes are desired, as represented by block 256. If no additional changes are desired, then a best fit placement of the different implant relative to the anatomical structure is determined by alignment software 230, as represented by block 120. If additional changes are desired, the user is prompted regarding whether to change constraints on the placement of the implant, as represented by block 250.

If the user selects to alter constraints on the implant, then the user through user input devices 222 provides additional constraints regarding the placement of the selected implant and/or updates existing constraints regarding the placement of the selected implant, as represented by block 258. Exemplary constraints include constraints relative to the anatomical structure and constraints relative to an orientation of the implant. Exemplary constraints relative to anatomical structure include a constraint that an interior flange of the implant remain below a natural flange of the anatomical structure, a constraint that an interior flange of the implant remain below set value, such as 2 millimeters, of a natural flange of the anatomical structure, in the case of a knee a constraint to maintain a "q" angle within a given range of values or a valgus value within a given range of values, resection depth of up to 10 mm, external femoral component rotation of between 0 degrees and 5 degrees, and other suitable constraints. Exemplary constraints relative to an orientation of the implant include a constraint that the implant is not flipped upside down.

In one embodiment, the user is presented with a plurality of constraints and simply selects additional constraints or modifies the variables for existing constraints with user input devices 222. Once the constraints have been altered, the user is prompted to determine if additional changes are desired, as represented by block 260. If no additional changes are desired, then a best fit placement of the selected implant relative to the anatomical structure based on the modified constraints is determined by alignment software 230, as represented by block 120. If additional changes are desired, the user is prompted regarding whether to manually adjust the placement of the implant, as represented by block 252.

If the user selects to manually adjust the placement of the implant relative to the anatomical structure, the user is able to translate and rotate the implant relative to the anatomical structure through user input devices 222. For example, the user may through user inputs 222 cause the implant to travel more posteriorly into the bone, to move more proximal, or rotate the implant internally or externally. Once the desired placement is achieved, as represented by block 262, alignment software 232 displays the adjusted placement and the anatomical structure as represented by block 242. The user may then decide if the placement of the implant is acceptable or to make additional changes to the implant selected or the placement of the implant, as represented by block 244.

In one embodiment, the implant to select from the library of implants 236 and the placement of the selected implant are initially determined based on a comparison of a contour of the current anatomical structure to a library of contours for other anatomical structures 242. For instance, a library of femur anatomical structures may be provided and the implant for use with a current femur may be selected and/or placed based on the implant selected and implanted in a femur of an anatomical structure in the library 242 which most closely matches the anatomical structure of the current femur.

Figure 8:
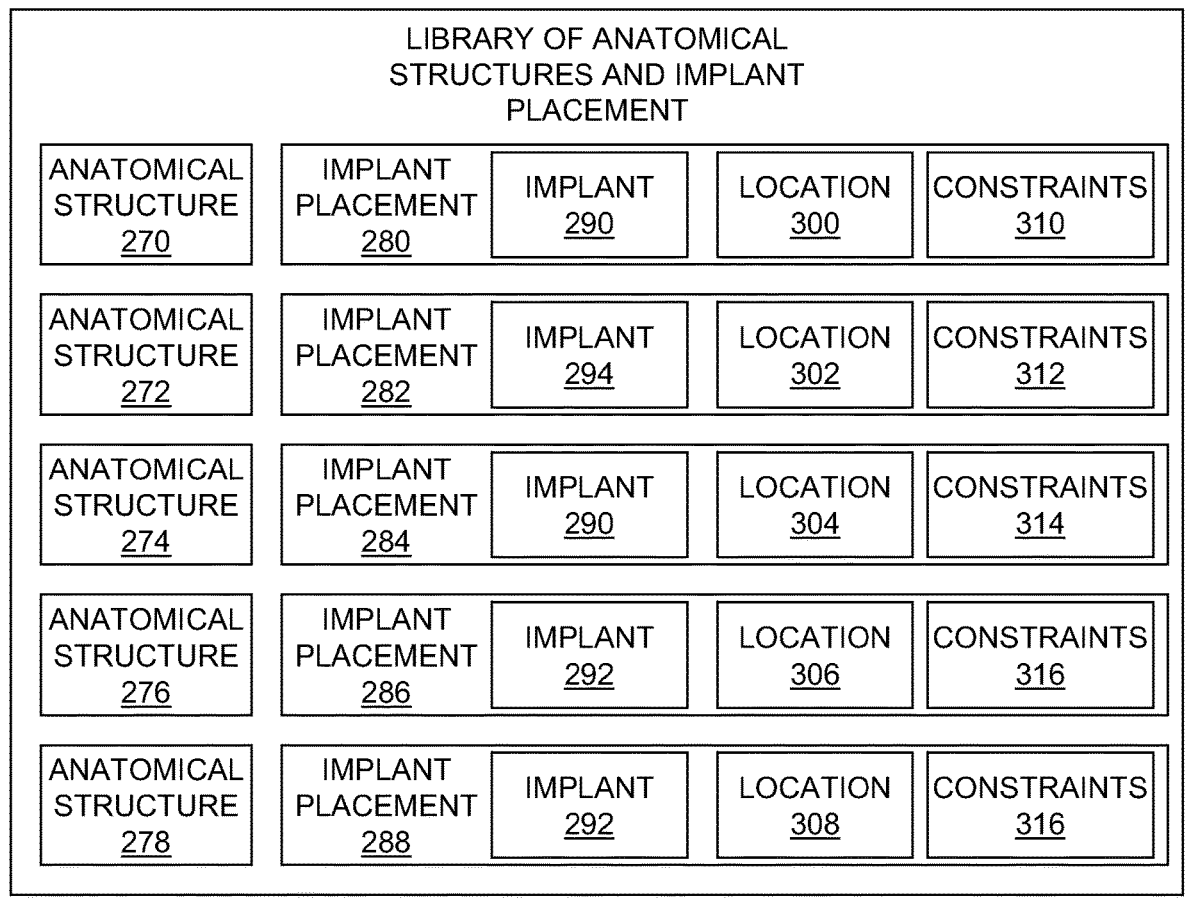
FIG. 8 represents a library of anatomical structures and placement locations.
Figure 9:
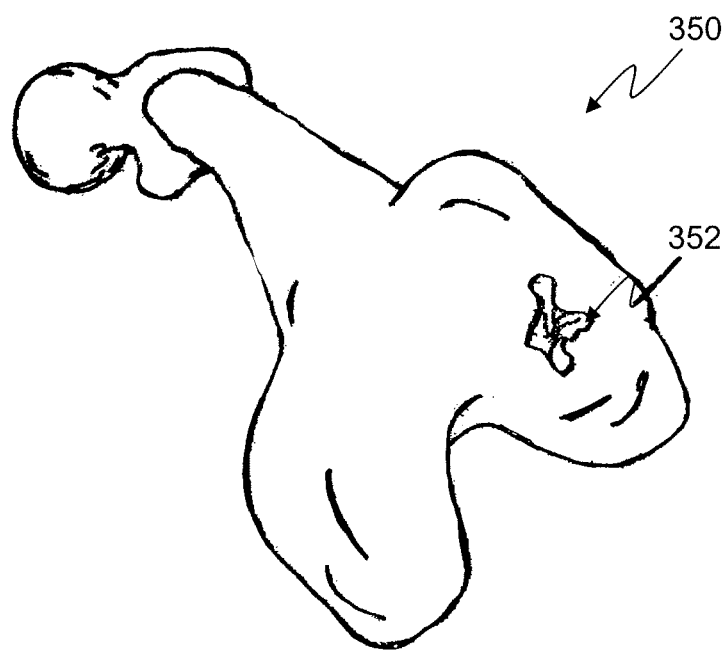
FIG. 9 represents a distal femur having a bone defect.
Figure 10:
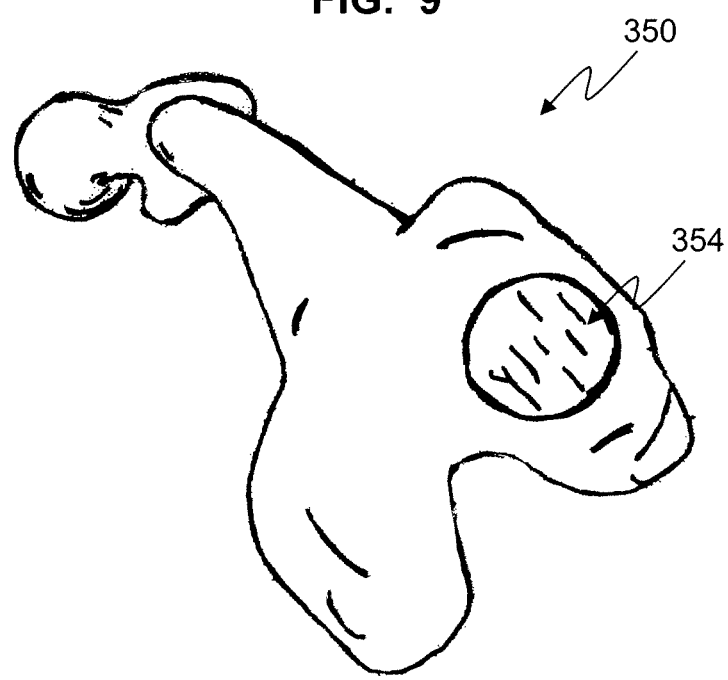
FIG. 10 represents the distal femur of FIG. 9 having a portion of the bone reamed out.
Figure 11:
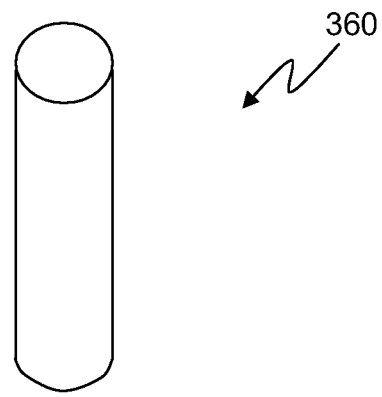
FIG. 11 represents a blank implant.
Figure 12:
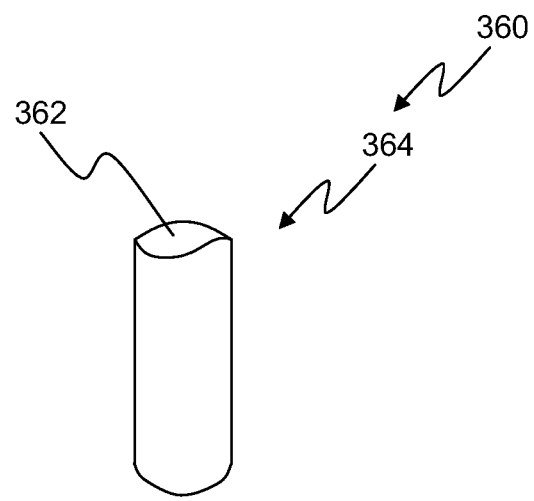
FIG. 12 represents the blank implant of FIG. 11 with a finished upper surface.

Referring to FIG. 8, a representation of the library of contours for other anatomical structures 242 is provided. Library 242 includes a plurality of anatomical structures 270-278 which have had orthopaedic surgery to include an implant in the past. For each anatomical structure 270-278, an implant placement 280-288, respectively, is provided. Each of implant placements 280-288 provide information regarding the implant which was implanted 290-294, location information for that implant 300-308, and the constraints placed on the location of the implant 310-316. Referring to FIG. 8, anatomical structures 270 and 274 each used the same implant 290 and anatomical structures 276 and 278 each used the same implant 292. Further, anatomical structures 276 and 278 each have the same set of constraints 316.

In one embodiment, alignment software 232 compares the current anatomical structure to anatomical structures 270-278 and selects the one anatomical structure which most closely matches the current anatomical structure. By way of example, assume that anatomical structure 274 is the closest match. Then alignment software 232 selects implant 290 and places implant 290 relative to the current anatomical structure based on location information 304 as a first representation of the best fit placement 120. The user may then alter the placement of the implant or change the implant as described herein.

In one embodiment, alignment software 232 compares the current anatomical structure to anatomical structures 270-278 and selects the one anatomical structure which most closely matches the current anatomical structure and has the same or closest set of constraints. By way of example, assume that anatomical structure 274 is the closest match, but has different constraints, while anatomical structure 270 has the same or nearly the same constraints as the current placement. In this situation, the alignment software 232 selects implant 290 and places implant 290 relative to the current anatomical structure based on location information 300 as a first representation of the best fit placement 120 because it more closely approximates the desired constraints of the current anatomical structure. The user may then alter the placement of the implant or change the implant as described herein.

Referring to FIGS. 9-12, another method of implanting a implant in an anatomical structure is shown. As described herein a contour of an anatomical structure 350 is obtained. The anatomical structure including a bone defect 352. In order to remove the bone defect, CAS system 200 and/or the surgeon removes the bone defect as generally represented by 354. In one embodiment, a mill 210 is used to remove the bone defect. A blank implant 360 may be secured to the anatomical structure 350 in the recess 354. The contour information regarding anatomical structure 350 is used to determine a shape 362 of a top portion 364 of blank implant 360. Shape 362 is machined to generally match the contour of anatomical structure 350. In one embodiment, shape 362 is machined after blank implant 360 is coupled to anatomical structure 350. In one embodiment, shape 362 is machined prior to blank implant 360 is coupled to anatomical structure 350.

In one embodiment related to knees, controller 202 by knowing the tension on the ligaments of the current anatomical structure may predict based on the placement of the selected implant what the effect would be on flexion of the joint with the implant coupled to the anatomical structure.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A method operating within a computer aided surgical (CAS) system, the method comprising:
   receiving, within the CAS system, identification of a region of a surface of an anatomical structure for replacement by an implant;
   acquiring, using data received from a tracking device within the CAS system tracking a pointer probe, a plurality of data points obtained as the pointer probe temporarily contacts at least a portion of the region of the surface of the anatomical structure, each data point of the plurality of data points representing a discrete location on the surface of the region; and
   approximating a surface contour of the region of the surface based on the plurality of data points at least in part by correlating each data point of the plurality of data points to a three-dimensional coordinate system generated by the CAS system.

2. The method of claim 1, wherein the acquiring the plurality of data points includes:
   receiving an indication that the pointer probe is positioned at a first position; and
   determining a first data point of the plurality of data points including a first coordinate of the first position.

3. The method of claim 2, wherein receiving the indication includes receiving a user generated input indicating the pointer probe is positioned within the portion of the surface of the anatomical structure.

4. The method of claim 2, wherein acquiring the plurality of data points includes:
   receiving a second indication that the pointer probe is positioned at a second position; and
   determining a second data point of the plurality of data points including a second coordinate of the second position.

5. The method of claim 4, wherein receiving the second indication includes receiving a second user generated input indicating the pointer probe is positioned in the second position within the portion on the surface of the anatomical structure.

6. The method of claim 4, wherein receiving the second indication includes receiving an indication of a predetermined time interval from acquisition of the first data point.

7. The method of claim 1, wherein acquiring the plurality of data points includes tracking the pointer probe location within a three-dimensional coordinate system, wherein each data point of the plurality of data points is a discrete location within the three-dimensional coordinate system.

8. The method of claim 1, further comprising selecting a first implant from a plurality of implants to repair a defect on the anatomical structure based at least in part on the surface contour.

9. The method of claim 8, wherein selecting the first implant is based on determining that, in comparison to other implants in the plurality of implants, the first implant includes a surface most closely matching the surface contour.

10. The method of claim 8, wherein the plurality of implants are selected from a library of implants based on each implant within the plurality of implants satisfying at least one constraint related to the anatomical structure.

11. A non-transitory computer-readable medium including instructions that, when executed by a computing device, cause the computing device to perform operations comprising:
    receiving, within the computing device, identification of a region of a surface of an anatomical structure for replacement by an implant;
    acquiring, using data received from a tracking device communicatively coupled to the computing device tracking a pointer probe, a plurality of data points obtained as the pointer probe temporarily contacts at least a portion of the region of the surface of the anatomical structure, each data point of the plurality of data points representing a discrete location on the surface of the region; and
    approximating a surface contour of the region of the surface based on the plurality of data points at least in part by correlating each data point of the plurality of data points to a three-dimensional coordinate system generated by the computing device.

12. The computer-readable medium of claim 11, wherein the acquiring the plurality of data points operation includes:
    receiving an indication to capture a first data point;
    determining, in response to the indication, the first data point of the plurality of data points, the first data point including a first coordinate within a three-dimensional coordinate system;
    receiving a second indication to capture a second data point; and
    determining, in response to the second indication, the second data point of the plurality of data points, the second data point including a second coordinate within the three-dimensional coordinate system.

13. The computer-readable medium of claim 12, wherein the indication is a user generated input.

14. The computer-readable medium of claim 12, wherein the second indication is a predetermined time interval from the capture of the first data point.

15. The computer-readable medium of claim 12, wherein the operations further include selecting a first implant from a plurality of implants to repair a defect on the anatomical structure based at least in part on the surface contour.

* * * * *